United States Patent
Weiss et al.

(10) Patent No.: US 12,040,066 B1
(45) Date of Patent: Jul. 16, 2024

(54) CLOUD-BASED METHODS AND SYSTEMS FOR PROVIDING ADAPTIVE PRESCRIPTION REMINDERS

(71) Applicant: WALGREEN CO., Deerfield, IL (US)

(72) Inventors: Benjamin Weiss, Chicago, IL (US); Ankur Jain, Chicago, IL (US); Kate Louise Paduchowski, Hamtramck, MI (US)

(73) Assignee: WALGREEN CO., Deerfield, IL (US)

( * ) Notice: Subject to any disclaimer, the term of this patent is extended or adjusted under 35 U.S.C. 154(b) by 479 days.

(21) Appl. No.: 16/895,157

(22) Filed: Jun. 8, 2020

(51) Int. Cl.
*G16H 20/13* (2018.01)
*G06F 9/4401* (2018.01)
*G16H 10/00* (2018.01)
*G16H 10/60* (2018.01)
*G16H 20/10* (2018.01)

(52) U.S. Cl.
CPC ........... *G16H 20/13* (2018.01); *G06F 9/4418* (2013.01); *G16H 10/60* (2018.01); *G16H 20/10* (2018.01); *G16H 10/00* (2018.01)

(58) Field of Classification Search
CPC ................................................ G06Q 50/20–26
See application file for complete search history.

(56) References Cited

U.S. PATENT DOCUMENTS

| | | | |
|---|---|---|---|
| 8,032,397 B2 * | 10/2011 | Lawless | G16H 40/67 705/2 |
| 11,245,691 B1 * | 2/2022 | Dods | G06F 18/23 |
| 2005/0267356 A1 * | 12/2005 | Ramasubramanian | A61J 1/03 600/411 |

(Continued)

OTHER PUBLICATIONS

Shin, Terence, "All Machine Learning Models Explained in 6 Minutes" Towards Data Science as downloaded from https://towardsdatascience.com/all-machine-learning-models-explained-in-6-minutes-9fe30ff6776a (Year: 2020).*

(Continued)

*Primary Examiner* — Neal Sereboff
(74) *Attorney, Agent, or Firm* — MARSHALL, GERSTEIN & BORUN LLP; Randall G. Rueth

(57) ABSTRACT

A computing system for adaptive prescription reminders includes a processor and a memory storing instructions that, when executed by the processor, cause the system to receive a fill event, generate an initial schedule, receive an medication consumption indication, generate an updated schedule using a trained machine learning model, cause the updated schedule to be displayed, and receive a patient confirmation. A computer-implemented method includes receiving a fill event, generating an initial schedule, receiving an medication consumption indication, generating an updated schedule using a trained machine learning model, causing the updated schedule to be displayed, and receiving a patient confirmation. A non-transitory computer readable medium includes program instructions that when executed, cause a computer to: receive a fill event, generate an initial schedule, receive an medication consumption indication, generate an updated schedule using a trained machine learning model, cause the updated schedule to be displayed, and receive a patient confirmation.

20 Claims, 7 Drawing Sheets

(56) References Cited

U.S. PATENT DOCUMENTS

| | | | | |
|---|---|---|---|---|
| 2007/0016443 A1* | 1/2007 | Wachman | G16H 20/10 | 600/300 |
| 2009/0134181 A1* | 5/2009 | Wachman | G16H 20/13 | 220/200 |
| 2010/0328099 A1* | 12/2010 | Wachman | G16H 40/67 | 340/870.07 |
| 2012/0160908 A1* | 6/2012 | Downey | G16H 20/13 | 235/375 |
| 2013/0090937 A1* | 4/2013 | Wright | G16H 40/67 | 705/2 |
| 2015/0174349 A1* | 6/2015 | Tunnell | A61M 15/009 | 128/200.14 |
| 2015/0283036 A1* | 10/2015 | Aggarwal | A61J 7/0436 | 206/534 |
| 2016/0203290 A1* | 7/2016 | An | G16H 40/67 | 705/2 |
| 2016/0324727 A1* | 11/2016 | Waugh | G16H 20/13 | |
| 2017/0068798 A1 | 3/2017 | Akinwale et al. | | |
| 2017/0293738 A1* | 10/2017 | Bender | G16H 10/60 | |
| 2018/0060517 A1* | 3/2018 | Bagwell | G16H 20/60 | |
| 2020/0098456 A1* | 3/2020 | Loscutoff | G16H 20/10 | |
| 2020/0350064 A1* | 11/2020 | Karedla | G06F 40/174 | |
| 2020/0411153 A1* | 12/2020 | Bagwell | A61J 7/0418 | |

OTHER PUBLICATIONS

U.S. Appl. No. 16/870,536, Derza, Automated Sig Code Translation Using Machine Learning, filed May 8, 2020.

\* cited by examiner

CLOUD-BASED METHODS AND SYSTEMS FOR PROVIDING ADAPTIVE PRESCRIPTION REMINDERS

CROSS-REFERENCED TO RELATED APPLICATION

The present application relates to U.S. patent application Ser. No. 16/870,536, filed May 8, 2020, entitled AUTOMATED SIG CODE TRANSLATION USING MACHINE LEARNING.

TECHNICAL FIELD

The present disclosure is generally directed to cloud-based methods and systems for providing adaptive prescription reminders to a pharmacy patient, and more specifically, for analyzing pharmacy data using machine learning to generate prescription schedules and reminder notifications.

BACKGROUND

Conventional pharmacy computing environments rely on centralized computing architectures and are, thus, severely limited. For example, in conventional systems, prescription data (e.g., a patient's list of prescribed medications, a medication schedule, etc.) may be stored exclusively in a device of the patient. Consequently, when the patient has multiple devices (e.g., a mobile phone and a tablet) such devices may be unable to communicate prescription data, leading to a lack of synchronization. Information such as a reminder cannot be shared between, for example, a computing application of the patient's mobile phone device and a computing application of the patient's tablet device. Patient devices thus include out-of-sync and/or redundant prescription data.

Centralized pharmacy computing environments further suffer from a lack of geographic flexibility. For example, a retailer may operate in multiple geographic regions within one country or distributed around the globe. Centralized environments do not allow the retailer to adjust operations to account for the variety of local laws and regulations in each region.

Another problem in conventional pharmacy computing environments is that the pharmacy retailer has little insight into the patient's activity after the patient picks up the filled prescription. Centralized computing environments may not provide the pharmacy retailer with information sufficient to determine whether the patient is adhering to the prescription instructions. For example, the pharmacy retailer cannot determine whether the patient is taking too much or too little of the medication. Such unknowns limit the ability of the pharmacy to assist the patient, except in very limited circumstances such as when the patient is physically visiting the pharmacy retail location.

Yet another drawback to conventional pharmacy computing environments is that all medications are assumed to relate to chronic (i.e., never ending) schedules, and are thus not able to account for medications that are taken for acute illness, for a period of time.

BRIEF SUMMARY

In one aspect, a pharmacy computing system for facilitating an adaptive reminder of a pharmacy prescription includes: one or more processors; and a memory storing instructions that, when executed by the one or more processors, cause the pharmacy computing system to: receive, from a retail pharmacy computing system, one or both of (i) a prescription refill event, and (ii) a prescription fill event corresponding to the pharmacy prescription, analyze the event corresponding to the pharmacy prescription to generate an initial prescription schedule, receive one or more indications of the patient's consumption of a medication corresponding to the pharmacy prescription, analyze the one or more indications using a trained machine learning model to generate an updated prescription schedule, cause the updated prescription schedule to be displayed in a graphical user interface of an application on the patient computing device, and receive an indication of confirmation with respect to the updated prescription schedule.

In another embodiment, a computer-implemented method for facilitating an adaptive reminder of a pharmacy prescription includes: receiving, from a retail pharmacy computing system, one or both of (i) a prescription refill event, and (ii) a prescription fill event corresponding to the pharmacy prescription, analyzing the event corresponding to the pharmacy prescription to generate an initial prescription schedule, receiving one or more indications of the patient's consumption of a medication corresponding to the pharmacy prescription, analyzing the one or more indications using a trained machine learning model to generate an updated prescription schedule, causing the updated prescription schedule to be displayed in a graphical user interface of an application on the patient computing device, and receiving an indication of confirmation with respect to the updated prescription schedule.

In yet another embodiment, a non-transitory computer readable medium contains program instructions that when executed, cause a computer to: receive, from a retail pharmacy computing system, one or both of (i) a prescription refill event, and (ii) a prescription fill event corresponding to the pharmacy prescription, analyze the event corresponding to the pharmacy prescription to generate an initial prescription schedule, receive one or more indications of the patient's consumption of a medication corresponding to the pharmacy prescription, analyze the one or more indications using a trained machine learning model to generate an updated prescription schedule, cause the updated prescription schedule to be displayed in a graphical user interface of an application on the patient computing device, and receive an indication of confirmation with respect to the updated prescription schedule.

BRIEF DESCRIPTION OF THE FIGURES

The figures described below depict various aspects of the system and methods disclosed therein. It should be understood that each figure depicts one embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

Figure 1:
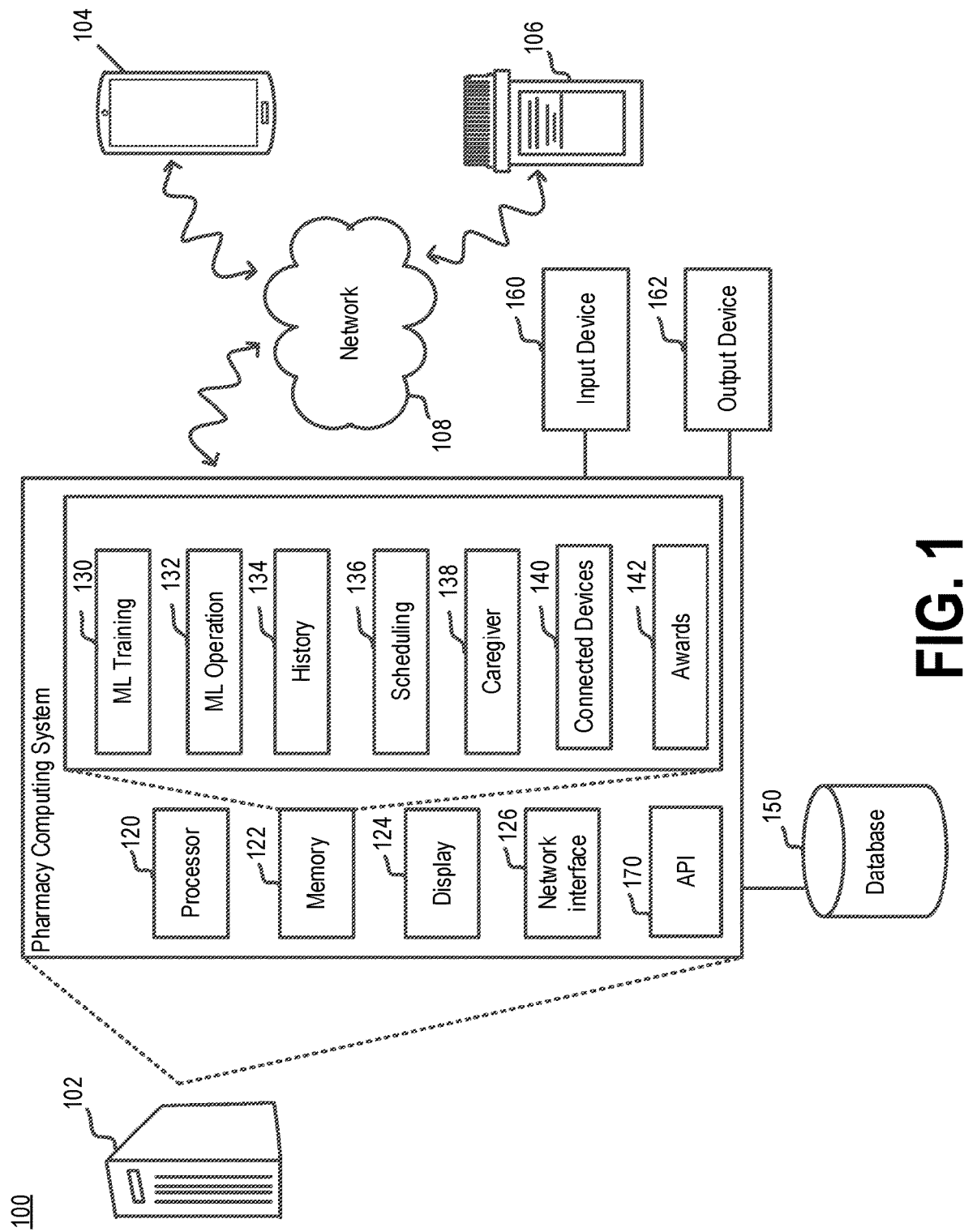
FIG. 1 depicts an exemplary computing environment in which techniques for cloud-based pharmacy computing methods and systems may be implemented, according to one embodiment.

The figures depict preferred embodiments for purposes of illustration only. One of ordinary skill in the art will readily recognize from the following discussion that alternative embodiments of the systems and methods illustrated herein may be employed without departing from the principles of the invention described herein.

DETAILED DESCRIPTION

Overview

The embodiments described herein relate to, inter alia, techniques for displaying and configuring pharmacy patient prescription reminders on behalf of pharmacy patients and/or caregivers. The present techniques include cloud computing platform techniques including tracking patient pharmacy data (e.g., medications, prescriptions, schedules, history, relationships, reports, etc.). The present techniques include application programming interfaces (APIs) for accessing the patient pharmacy data. The present techniques advantageously systematize access to patient pharmacy data, adding much needed implementation flexibility, and allowing new front-end applications to be plugged into the cloud computing platform with less development overhead.

The cloud computing platform techniques include a pill reminder platform including APIs for connecting pharmacy computing application to computing networks, enabling third-party integrations; automated medication setup when the patient fills a prescription; caregiver tools connecting patients and their caregivers; adaptive reminders that leverage machine learning to intelligently adapt to the patient's real medication schedule; refill reminders that automatically track the amount of medication remaining in a package (e.g., a pill bottle); and automated tracking of patient consumption of over-the-counter (OTC) medications and vitamins.

The present techniques include a host of benefits to pharmacy patients. For example, patients benefit by receiving free chronic disease medication management (e.g., pill reminders), resulting in improved prescription adherence and driving improved health incomes. Pharmacy patients also benefit from synchronized access to pharmacy data across multiple devices. Pharmacy patients benefit from new modes of communication with caregivers, eliminating friction.

In general, the present techniques extend the pharmacy journey outside the four walls of the pharmacy by, for example, generating notifications/alerts throughout the day based on a prescription schedule, and for preemptively notifying the patient when a medication is running low and in need of a refill. Thus, the present techniques advantageously create a positive feedback loop between the patient and pharmacy sorely lacking in conventional pharmacy computing systems.

Some embodiments of the present techniques include analyzing sig codes. SIGs or sig codes are shorthand abbreviations used by medical professionals (e.g., physicians, pharmacists, pharmacy technicians, etc.) to specify directions for use of a medicine. Sig codes are commonly used to encode instructions for a patient to follow during a prescription regimen, and may be printed on packaging (e.g., in an information sheet accompanying a prescription, on a bottle, inhaler, etc.) A physician may specify a compressed sig code when authoring a medical prescription or script. In some cases, a pharmacy technician or pharmacist may convert the compressed sig code to an expanded sig code that may be more readable by a patient. The term "sig" is an abbreviation for the Latin term "signa," meaning mark, stamp, designation or label. Sig codes may be used to specify a number of attributes of a prescription, including a quantity, a dosing form/route of administration, a frequency, a duration, etc.

In some embodiments, the present techniques may receive an unstructured or structured data representation of a sig code. For example, the structured data corresponding to a sig code may be expressed using JavaScript Object Notation (JSON), eXtensible Markup Language (XML), etc. The structured and/or unstructured representation of the sig code may be generated by an upstream process (e.g., a trained machine learning model). The sig code representation may include information conventionally present in sig codes, such as an identification of a medication and instructions for taking the medication (e.g., a quantity, a frequency, a drug form, a route of administration, etc.). The scheduling aspects of the present techniques may include interpolating the sig code instructions into an initial schedule. The initial schedule may be based on a default schedule for the prescription. Herein, the terms "provider", "prescriber", and "physician" may be used interchangeably. A "patient" generally refers to a customer of the pharmacy to whom medications are prescribed.

Exemplary Computing Environment

FIG. 1 depicts an exemplary computing environment 100 in which techniques for automated prescription reminder scheduling using machine learning, according to an embodiment. The environment 100 includes a pharmacy computing system 102, a patient computing device 104 and a connected prescription device 106. In the depicted embodiment, the pharmacy computing system 102, the patient computing device 104 and the connected prescription device 106 are communicatively coupled via a network 108.

The pharmacy computing system 102 may be located within a pharmacy or may be remote to the pharmacy. In some embodiments, multiple pharmacy computing systems 102 may be implemented in the pharmacy and/or remote to the pharmacy. Generally, a user (e.g., a pharmacist, a medical doctor, a pharmacy technician, etc.) may access the pharmacy computing system 102 to access pharmacy information for the provision of service to a pharmacy customer.

The pharmacy computing system 102 may be an individual server, a group (e.g., cluster) of multiple servers, or another suitable type of computing device or system (e.g., a collection of cloud computing resources). One or more components of the pharmacy computing system 102 may be provided by virtual instances (e.g., cloud-based virtualization services).

The pharmacy computing system 102 includes a processor 120 that may include any suitable number of processors and/or processor types, such as CPUs and one or more graphics processing units (GPUs). Generally, the processor 120 is configured to execute software instructions stored in a memory 122. The memory 122 may include one or more persistent memories (e.g., a hard drive/solid state memory) and stores one or more sets of computer executable instructions/modules, including a machine learning training module 130, a machine learning operation module 132, a history module 134, a scheduling module 136, a caregiver module 138, a connected devices module 140, and a rewards module 142 as described in more detail below.

The pharmacy computing system 102 further includes a network interface controller (NIC) 124 that may include any suitable network interface controller(s), such as wired/wireless controllers (e.g., Ethernet controllers). The NIC 124 facilitates bidirectional/multiplexed networking over the network 108 between the pharmacy computing system 102 other components of the environment 100 (e.g., the patient computing device 104 and/or the connected prescription device 106).

The pharmacy computing system 102 may include a pharmacy database 150, which may be implemented as a relational database computing system (RDBMS). For example, the pharmacy database 150 may include one or more structured query language (SQL) database, a NoSQL database, a flat file storage system, or any other suitable data storage system/configuration. In general, the pharmacy database 150 may store prescription information related to patients, patient profile information, ML training data, ML models and/or initialization parameters and/or outputs generated by one or more ML models. The pharmacy database 150 may receive its contents from the pharmacy computing system 102, the patient computing device 104 and/or the connected device 106. In some embodiments, the pharmacy database 150 may be located remote from the pharmacy computing system 102 and accessed via the network 108. The pharmacy computing system 102 may be associated with (e.g., owned/operated by) a company that sells commercial, medical, financial, etc. products and/or services, and/or an entity that provides prescription medicine to patients. The modules stored in the memory 122 of the pharmacy computing system 102 include respective sets of computer-executable instructions for performing specific functions. For example, one or more components of the environment 100 may be physically located within a retail pharmacy, while others are located within a data center remote from the retail pharmacy.

The machine learning training module 130 may include instructions executed by the processor 120 for initializing and training one or more machine learning models. In general, the ML training module 130 may train models by, inter alia, establishing a network architecture, or topology, and adding layers that may be associated with one or more activation functions (e.g., a rectified linear unit, softmax, etc.), loss functions and/or optimization functions. Multiple different types of artificial neural networks may be employed, including without limitation, recurrent neural networks, convolutional neural networks, and deep learning neural networks. Data sets used to train the artificial neural network(s) may be divided into training, validation, and testing subsets; these subsets may be encoded in an N-dimensional tensor, array, matrix, or other suitable data structures. Training may be performed by iteratively training the network using labeled training samples. Training of the artificial neural network may produce byproduct weights, or parameters which may be initialized to random values. The weights may be modified as the network is iteratively trained, by using one of several gradient descent algorithms, to reduce loss and to cause the values output by the network to converge to expected, or "learned", values. In an embodiment, a regression neural network may be selected which lacks an activation function, wherein input data may be normalized by mean centering, to determine loss and quantify the accuracy of outputs. Such normalization may use a mean squared error loss function and mean absolute error. The artificial neural network model may be validated and cross-validated using standard techniques such as hold-out, K-fold, etc. In some embodiments, multiple artificial neural networks may be separately trained and operated, and/or separately trained and operated in conjunction.

A processor or a processing element may be trained using supervised or unsupervised machine learning, and the machine learning program may employ a neural network, which may be a convolutional neural network, a deep learning neural network, or a combined learning module or program that learns in two or more fields or areas of interest. Machine learning may involve identifying and recognizing patterns in existing data in order to facilitate making predictions for subsequent data (e.g., de novo prescription schedules based on analysis of historical patient behavior/take times). Models may be created based upon example inputs in order to make valid and reliable predictions for novel inputs. In some embodiments, the machine learning training module 130 may train a linear regression or logistic regression model. In some embodiments, the training may encode patient preferences relative to the day of the week. For example, some patients may sleep in on weekends. As such, the machine learning training module 130 may include instructions for adjusting prescription scheduling modeling to a later start time on Saturdays, Sundays and holidays.

The ML operation module 132 may load a model (e.g., a deep learning model) trained by the ML training module 130 from the memory 122 or another location. For example, the ML operation module 132 may load a trained ML model and pass a series of parameters (e.g., one or more patient prescription take times). For example, the ML operation module 132 may receive/retrieve a list of take times from the database 150. The ML operation module 132 may receive from the trained ML model an output corresponding to a new suggested take time, based on the ML model analyzing the patient's historical take times, for example.

The history module 134 may include a set of computer-executable instructions for collecting and storing patient take times. For example, the instructions may receive/retrieve an HTTP request from the patient computing device 106 including a timestamp reflecting a take time of a medication, indicating that the patient took the medication at the take time. The history module 134 may store the take time in association with the patient identifier in the database 150, in some embodiments. Over time, the history module 134 builds up a log of take times corresponding to patients that may be queried/analyzed by other modules (e.g., the ML operation module 132). The history module 134 may include instructions for retrieving a patient profile from the database 150. The patient profile may include one or more patient identifiers (e.g., patient name, date of birth, telephone, etc.) and electronic health record (EHR) information. The patient profile may further include a list of the patient's past and current prescriptions.

Figure 4A:
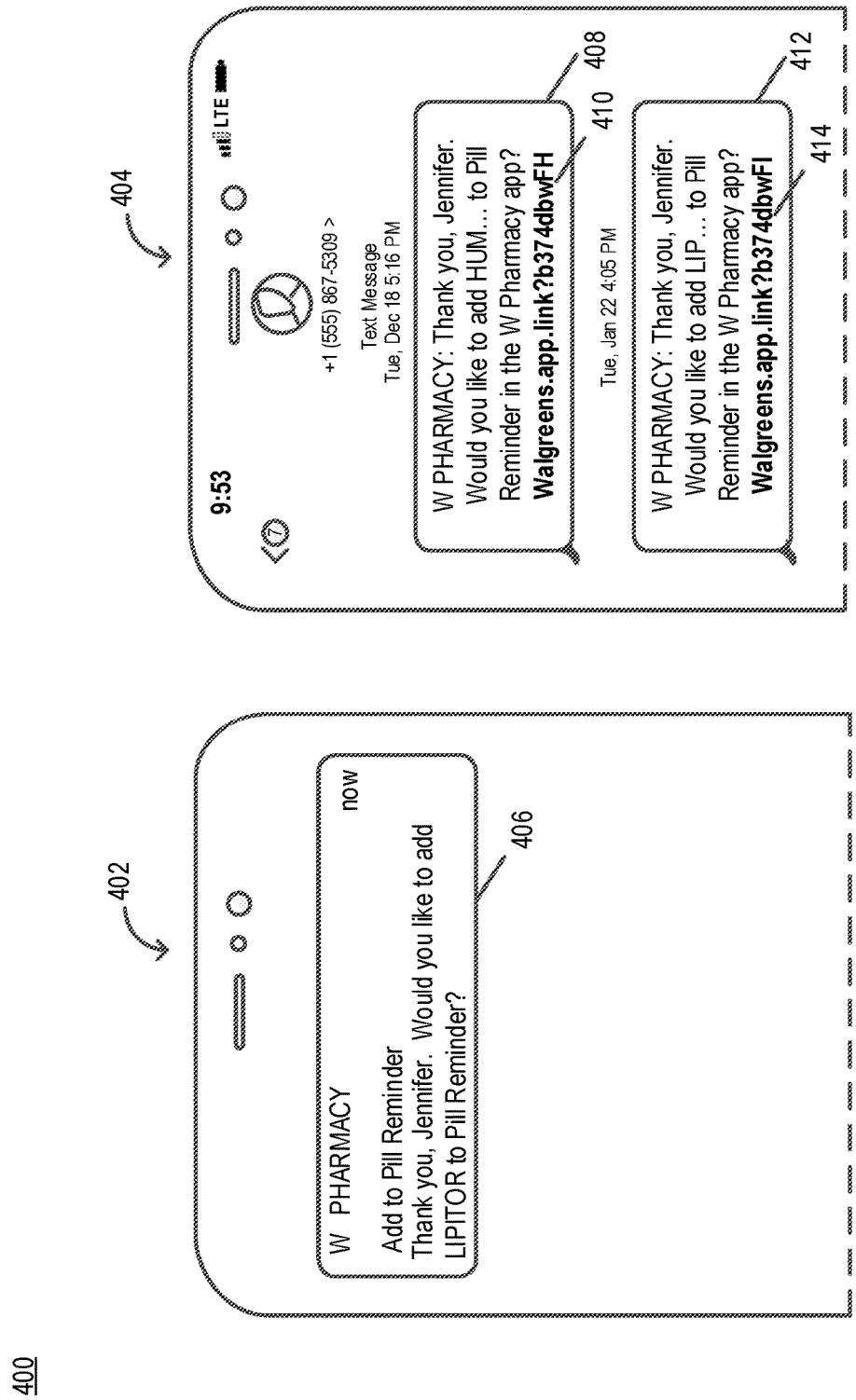
FIG. 4A depicts exemplary graphical user interfaces for displaying a prescription reminder setup notification and/or for receiving patient prescription reminder confirmation, according to one embodiment.
Figure 4B:
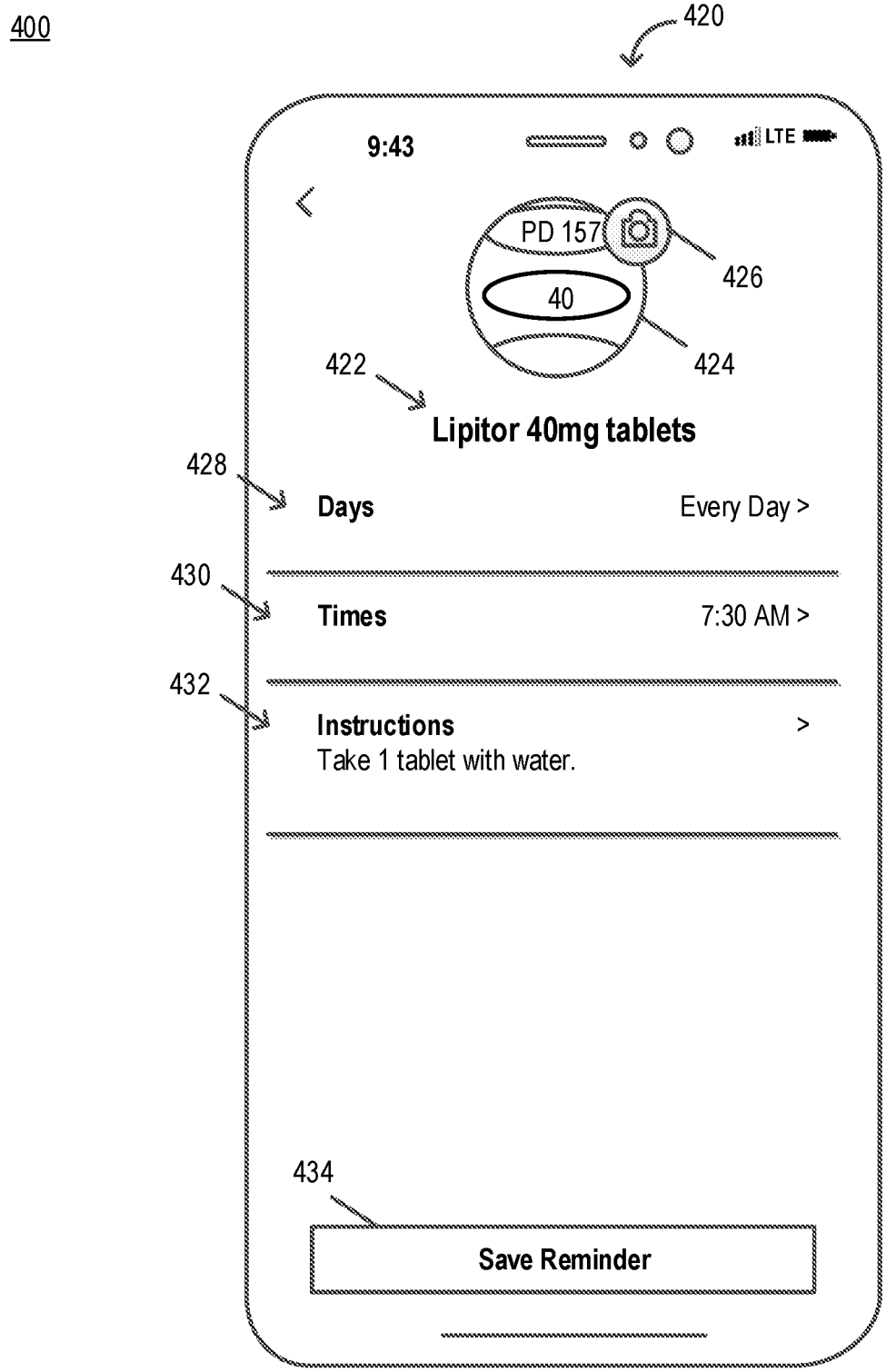
FIG. 4B depicts an exemplary graphical user interface for displaying a prescription reminder, according to one embodiment.
Figure 4C:
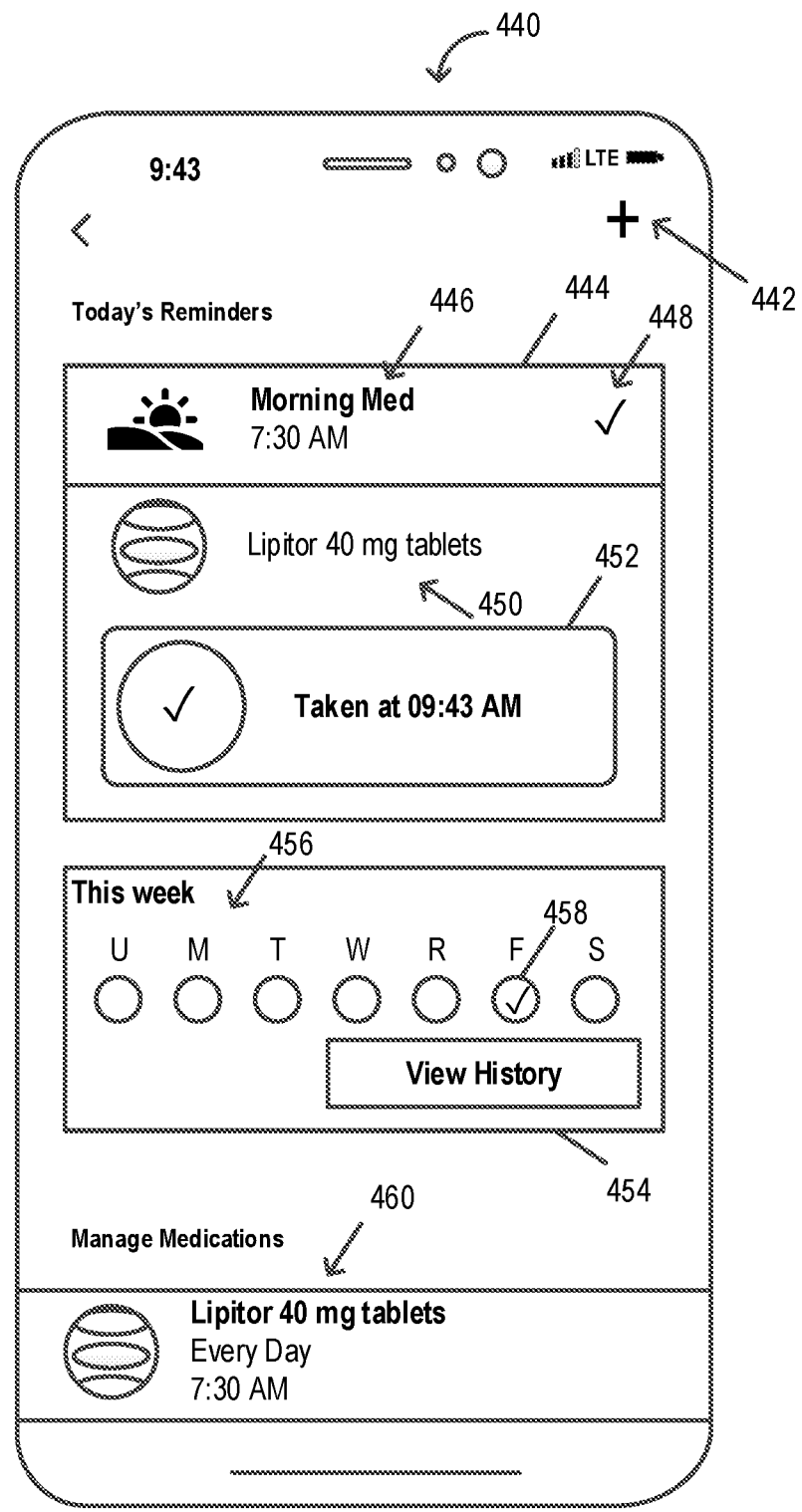
FIG. 4C depicts an exemplary graphical user interface for displaying a list of daily prescription reminders, according to one embodiment.

The scheduling module 136 may include instructions for analyzing information to create an initial prescription schedule. For example, the scheduling module 136 may analyze an input sig code. The scheduling module 136 may generate an electronic calendar object (e.g., a calendar formatted according to the Internet Calendaring and Scheduling Core Object Specification). Herein the term "prescription schedule" may include the electronic calendar object. The scheduling module 136 may configure the calendar object such that the patient will take the prescribed quantity (e.g., 2) of a drug form (e.g., a tablet) according to a set of instructions (e.g., take) at the prescribed frequency (e.g., four times daily). The schedule may be based on a default for the prescription. For example, the scheduling module 136 instructions may analyze the output and fill in a title of the calendar object with a text title corresponding to the expanded sig code (e.g., "take two tablets four times daily"). For example, the instructions may configure the default calendar object to include four reminders, spaced three hours apart, during predetermined waking hours (e.g., from 8 am and 8 pm). The scheduling module 136 may receive and process patient requests to update/set prescription reminders, as shown in FIG. 4A, FIG. 4B and FIG. 4C. The scheduling module 163 may store prescription reminders corresponding to electronic calendar objects in the database 150 in some embodiments. The initial/default prescription schedule may be modified by the output of the ML operation module 132, to better reflect the patient's actual consumption patterns.

The caregiver module 138 includes computer-executable instructions that when executed, cause the pharmacy computing system 102 to manage one or more patient-caregiver relationships. Specifically, each patient may delegate authority/permission to one or more caregivers. The caregiver permission may allow the caregiver to view some or all of the medication prescriptions associated with the patient's profile. The caregiver may use a computing device such as the device 104 (e.g., a caregiver computing device 104). The caregiver permission may allow the caregiver to manage medications and to schedule reminders on behalf of the patient. In some embodiments, the patient may use the patient computing device 104 to send a caregiver invitation to the one or more caretakers. The invitation may include a link to the pharmacy computing system. In some embodiments, the caregiver module 138 may include levels of permission that allow the patient to mask the names of medications that the patient is taking. In some embodiments, the caregiver may view all information, including the history of medications taken. The caregiver may also subscribe to receive reminders for the patient, as discussed herein. In some embodiments, the caregiver module 138 may generate a missed dosage notification when the patient does not take a medication at a scheduled time. The caregiver module 138 may transmit the notification to the patient.

The caregiver module 138 may enable access to a respective set of permissions for the patient and the one or more caregivers. The patient permissions may include basic permissions allowing the patient to view, create and edit medications; view, create and edit reminders; receive reminder notifications; mark medications as taken, skipped, discontinued, etc.; view and edit take history; view adherence reports; delegate one or more caregivers; and revoke the one or more caregivers. The patient permissions may further include limited permissions that correspond to a subset of the basic permissions. The patient may access the basic and remote permissions via a GUI, as discussed below. The permissions may be stored in the database 150, for example. The caregiver permissions may include enhanced permissions allowing the caregiver to create and edit medications; create and edit reminders; edit take history; receive reminder notifications; mark medications taken, skipped, discontinued, etc.; and restrict patient create/edit permissions. In some embodiments, the caregiver permissions may include a subset of the enhanced permissions.

The connected devices module 140 may include a set of computer-executable instructions for accessing one or more connected devices (e.g., a smart pill bottle, a smart medication organizer, etc.). The instructions may correspond to code authored by the pharmacy and/or client libraries (e.g., programming language bindings) provided by third parties (e.g., a software development kit (SDK)) for particular connected devices. In some embodiments, the connected devices module 140 may include instructions for accessing voice-enabled devices (e.g., an Amazon Alexa device, a Google Assistant device, etc.). The connected devices module 140 may include instructions for authorizing voice-enabled connected device to access information, and for transmitting reminders to the patient via one or more voice-enabled channels. For example, in an embodiment, the patient may authorize the voice-enabled device to issue reminders via a speaker of the connected device 106. The connected devices module 140 may receive an event corresponding to a take event when the patient/caregiver performs a remote action (e.g., opens a connected bottle cap).

In some embodiments, the awards module 142 may include a set of computer-executable instructions generating adherence awards. For example, the awards module 142 may periodically analyze patient prescription history via the history module 134. When the awards module 142 determines that the patient has consistently taken a medication for a predetermined time period (e.g., one week) the awards module 142 may issue a reward to the patient via a notification (e.g., a push message). The reward may be an encouragement in the form of a written message, a coupon, a monetary reward, etc. For example, the adherence module 142 may include instructions for awarding earned points to the patient for each day that the patient successfully marks all scheduled medications as taken for that day. The awards module 142 may generate daily notifications corresponding to the awarded points. In some embodiments, the awards module 142 may award extra rewards to the patient when the patient achieves a streak (i.e., adherence over a period of time). For example, streak awards may be awarded at 30 days, 60 days, 90 days, one year, two years, three years, etc.

In some embodiments, the awards module 142 may include instructions for generating a patient adherence report. For example, the patient adherence report may include graphical representations of patient adherence relating to one or more prescribed medications, wherein adherence is determined according to the prescription consumption history collected by the pharmacy computing system 102.

The pharmacy computing system 102 may include an input device 160 and an output device 162 that allow the user (e.g., the pharmacist) to access (i.e., provide input to and perceive outputs of) the pharmacy computing system 102. The input device 160 includes one or more components to facilitate the pharmacy computing system 102 to accept input from the user. For example, the input device 160 may include a keyboard and/or a microphone, with associated software (e.g., a driver/firmware). The output device 162 may include any suitable display technology (e.g., LED, OLED, LCD, etc.) for displaying information. In some embodiments, the input device 160 and the output device 162 may be integrated (e.g., in a touchscreen display). Generally, the input device 160 and the display device 162 combine to enable the user to interact with the pharmacy computing system 102.

The pharmacy computing system 102 may include an application programming interface (API) 170 by which another component and/or a third party (e.g., a customer of the proprietor of the pharmacy computing system 102) may access the pharmacy computing system 102. The API 170 may be implemented as an endpoint accessible via a web service protocol, such as representational state transfer (REST), Simple Object Access Protocol (SOAP), JavaScript Object Notation (JSON), etc. For example, an API client (e.g., a remote computing device) may access the API 170 by submitting an HTTP response including a patient prescription. The API 170 may pass the submitted HTTP response to a module of the pharmacy computing system 102 (e.g., the scheduling module 136). The API 170 may return an output via HTTP to the API client.

The patient computing device 104 may be any suitable device, such as a smart phone, a tablet, a desktop computer, etc. The patient may receive information (e.g., an electronic calendar object, prescription refill notifications, prescription refill reminders, etc.) via the patient computing device 104 via the network 108. The patient computing device 104 may include a processor and a memory including computer-executable instructions (e.g., instructions corresponding to a mobile computing application) that when executed, cause the received information to be displayed in a display screen of the patient computing device 104. The pharmacy computing system 102 may be communicatively coupled to other components in the environment 100 (e.g., the patient computing device 104 and/or the connected device 106) via the network 108. While FIG. 1 depicts one patient computing device 104, any number of patient computing devices 104 may be included in the environment 100, according to some embodiments. The patient computing device 104 may connect to one or more connected devices 106 (e.g., a smart pill bottle) via a suitable mechanism (e.g., via wireless Bluetooth pairing). The patient computing device 104 may receive event information (e.g., a bottle cap opened event) from the connected device 106. The patient computing device 104 may transmit the event via the network 108 to the pharmacy computing device 102, for example.

Generally, the pharmacy connected device 106 may be any suitable connected device, such as a smart medication bottle, a smart medication (e.g., pill) dispenser, a smart pill organizer, etc. The patient may pair the connected device 106 to the patient's account using the application executing in the patient device 104. Once paired, the pharmacy connected device 106 may transmit device status information (e.g., bottle cap opened, pill taken, quantity remaining, etc.) via the network 108 to the connected devices module 140. The connected devices module 140 may analyze the transmitted device status information and store the status update in the database 150, in association with the patient's profile. Thus, the pharmacy connected device 106 may function to store patient prescription take information in a way that does not require the patient to explicitly mark the prescription as taken. The device status information may be analyzed by, for example, a trained ML model using the ML operation module 132, in some embodiments.

The network 108 may be a single communication network, or may include multiple communication networks of one or more types (e.g., one or more wired and/or wireless local area networks (LANs), and/or one or more wired and/or wireless wide area networks (WANs) such as the Internet). The network 108 may enable bidirectional communication between the pharmacy computing system 102, the patient computing device 104 and the physician computing system 104.

In operation, the patient may fill or refill one or more prescriptions, for example, by visiting a retail pharmacy, placing an online order using the patient computing device 104, etc. In some embodiments, the pharmacy may be an online/virtual pharmacy or distribution center not accessible to the public. The pharmacy may include storage for medications and products, including restricted-access locations for storing controlled substances (e.g., narcotics) and refrigerated storage for perishable medications.

The pharmacy computing system 102 may modify the history of the patient in the database 150, noting that the patient refill/fill has taken place. In some embodiments, the pharmacy employee (e.g., pharmacist, pharmacy technician, clerk, etc.) may enter information into the pharmacy computing system via the input device 160, creating a record of the fill/refill via the history module 134. The scheduling module 136 may include a set of computer-executable instructions for causing one or more notifications to be transmitted to the mobile computing device 104 of the patient when the fill/refill occurs. In some embodiments, the notification may be transmitted after a predetermined amount of time has passed after the fill/refill. The notification mechanics and exemplary graphical user interfaces for notifications and scheduling are discussed further below. The notification may include a message prompting the patient to accept a default/initial schedule for the prescription corresponding to the patient's filled prescription. The schedule may be based on the patient's existing schedules (e.g., so that the patient's consumption of multiple medications is synchronized within the schedule). In some cases, the schedule may be automatically set without patient opt-in. In other embodiments, the patient may opt-in.

Once the patient opts-in, an application executing within the mobile computing device 104 of the patient may display one or more medication schedules (e.g., a daily schedule) to the patient. The application may accept an indication from the patient that the patient has taken the medication at a date/time. The application may transmit the take indication to the pharmacy computing system 102 for storage. As noted, in some embodiments, medication taken indications may be generated automatically by the pharmacy connected device 106. The application may display one or more graphical user interfaces allowing the patient/caregiver to view and/or adjust the patient's one or more medication schedules. In some embodiments, the application may automatically adjust the patient's default/initial schedules based on machine learning analysis of the patient's medication taken history.

In some embodiments, the pharmacy computing system 102 may be further used by the patient and/or one or more caregivers of the patient to assign/revoke permission to the one or more caregivers.

Exemplary Cloud Computing Architecture

Figure 2:
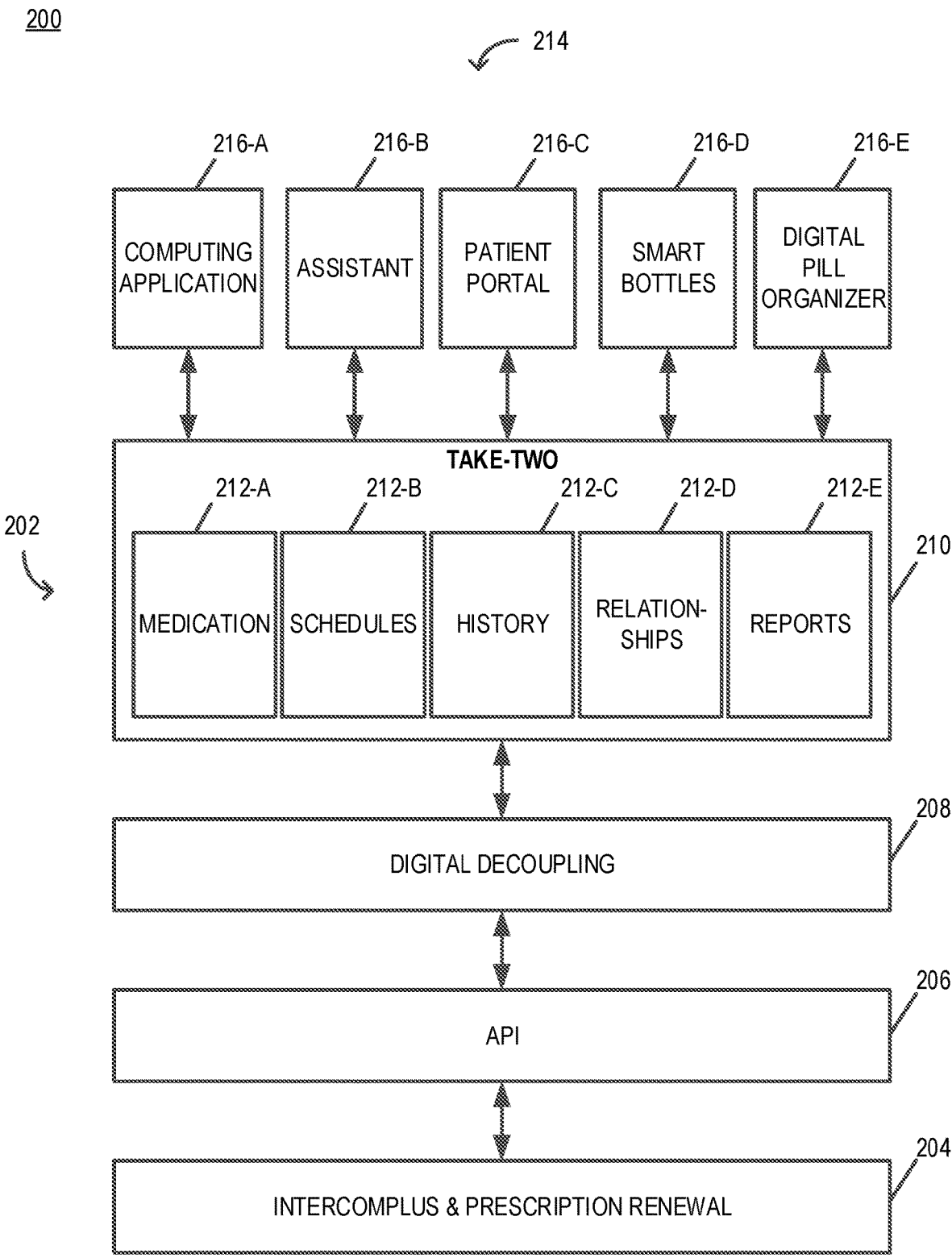
FIG. 2 depicts an exemplary block diagram of a cloud computing architecture, according to one embodiment.

FIG. 2 depicts an exemplary block diagram of a cloud computing architecture 200, according to one embodiment. The cloud computing architecture 200 may include a plurality of computing layers 202. The layers 202 may be implemented in one or more computing devices, such as the pharmacy computing system 102 of FIG. 1. For example, the layers 202 may include a retail pharmacy computing system layer 204 (e.g., Walgreen Company's proprietary Intercom Plus (IC+) computing system).

The retail pharmacy computing system layer 204 may include core pharmacy and internal source-of-record systems providing underlying pharmacy data and events, enabling other layers to track patient prescriptions. The retail pharmacy computing system layer 204 may communicate with one or more of the layers 202 via one or more APIs 206.

The APIs 206 may be implemented using any suitable computing techniques/technologies (e.g., representational state transfer (REST), simple object access protocol (SOAP), etc.). The retail pharmacy computing system layer 204 may allow medical professionals (e.g., a pharmacist, technician, etc.) to receive and/or transmit pharmacy data for filling prescriptions. The APIs 206 are bidirectional, allowing data to be written back to the retail pharmacy computing system layer 204. For example, when the patient/caregiver initiates a prescription refill, another layer within the cloud computing architecture 200 may initiate an API call via the APIs 206 for updating the patient's corresponding pharmacy data within the retail pharmacy computing system layer 204.

layer 210 may correspond to a cloud-based platform that serves as the system of record for everything that happens once the patient leaves the pharmacy with the patient's medication in hand. For example, the take-two layer 210 may keep track of the patient's medications, including OTC and third-party prescriptions, the patient's medication schedules, the patient's take history, the patient's caregiver relationship(s) and attendant access controls, and analytical reports derived from the patient's history.

The take-two layer 210 may implement the patient tracking features using a plurality of sub-layers for performing asynchronous functions. In some embodiments, the sub-layers may be implemented as independent computing modules within the memory 122 of the pharmacy computing system 102. The sub-layers may include a medications layer 212-A, a schedules layer 212-B, a history layer 202-C, a relationships layer 212-D, and a reports layer 212-E. Each of the sub-layers within the take-two layer 210 may correspond to API calls for accessing and/or retrieving data.

For example, the take-two layer 210 sub-layers may correspond, respectively, to the following API calls:

| HTTP Method | Endpoint | Description |
| --- | --- | --- |
| GET | Medications | Get patient's current medications |
| POST | createMedication | Add a new medication |
| POST | editMedication | Edit an existing medication's details |
| GET | Schedule | Get patient's reminder schedule |
| POST | Schedule | Update/modify patient's reminder schedule |
| GET | History | Retrieve patient's take history |
| POST | markReminder | Set reminder status |
| GET | Relationships | Retrieve patient's caregiver(s) and caregiver detail |
| POST | Relationships | Create/update patient's caregiver(s) and caregiver detail |
| GET | Reports | Retrieve report (e.g., adherence) |

The retail pharmacy computing system layer 204 may generate one or more events. For example, the retail pharmacy computing system layer 204 may generate an event when the patient picks up a prescription. The event may be a digital object corresponding to the event and may include event information/parameters as described above. The retail pharmacy computing system layer 204 may broadcast the generated event to other computing systems and/or layers (e.g., via multicast). The retail pharmacy computing system layer 204 may be remote from other computing assets of the computing environment 100 and may be communicatively coupled (e.g., by the APIs 206) to other layers/assets via the network 108. For example, the retail pharmacy computing system layer 204 may be communicatively coupled to a digital decoupling layer 208.

The digital decoupling layer 208 may include computer-executable instructions for processing the one or more events. For example, the digital decoupling layer 208 may be implemented using an asynchronous messaging service for decoupling an event generator (e.g., the retail pharmacy computing system layer 204) from an event processor (e.g., the decoupling layer 208). In some embodiments the message service may use the Publish-Subscribe (i.e., Pub/Sub) design pattern. A third-party Pub/Sub interface may be implemented in some embodiments. The digital decoupling layer 208 may enable one or more other layers to subscribe to events according to one or more event criteria (e.g., by event type, event origin, event severity, etc.).

For example, the computing layers 202 may include a take-two layer 210. In some embodiments, the take-two In some embodiments, one or more of the above endpoints may accept and/or require one or more parameters, that may differ according to the method used. For example, the createMedication endpoint may require a medication name, dosage type, form, etc. The Schedule endpoint may require a patient identifier, for example, when HTTP GET is used. The Schedule endpoint may require a list of scheduling-related parameters (e.g., duration, begin time, end time, etc.) when the HTTP POST method is used. In some embodiments, more or fewer endpoints may be used. Each of the endpoints may be subject to access control and/or encryption techniques. In still further embodiments, protocols other than HTTP may be used to implement the one or more API calls corresponding to the respective sub-layers.

The present technique advantageously improve conventional pharmacy computing systems by taking into account medication end dates. As noted, conventional pharmacy computing systems may assume that all medications are chronic. The present techniques support acute medication uses cases (e.g., an antibiotic) that may be taken for a short period of time (e.g., five to seven days). Specifically, the schedules layer 212-B may include instructions for allowing manual and automatic medication API calls to include a medication end date parameter.

The API endpoints may be accessible to other of the computing layers 202. For example, the cloud computing architecture 200 includes one or more front-end sub-layers 214. The front-end sub-layers 214 include a mobile computing application front-end layer 216-A, a voice assistant front-end layer 216-B, a patient portal front-end layer 216-

C, a smart bottle front-end layer 216-D and a digital pill organizer front-end layer 216-E. In some embodiments, more or fewer front-end layers 214 may be included. Each of the front-end sub-layers 214 may access one or more of the sub-layers of the take-two layer 210. The access may be asynchronous and concurrent with respect to each of the front-end sub-layers 214, alone and/or in combination, in some embodiments. The layers 216 may correspond to modules of the memory 122 of FIG. 1, in some embodiments.

The mobile application front-end layer 216-A may access (i.e., retrieve and/or modify) the medications layer 212-A. The access may be performed in response to input of the patient, in some embodiments. The mobile application front-end layer 216-A may simultaneously request information from the history layer 212-C. The voice assistant front-end layer 216-B may access the schedules layer 212-B, for example, in response to a vocal utterance of the patient and/or according to a pre-determined (i.e., default/initial) schedule. For example, the front-end layer 216-B may periodically access the medication schedules of the patient to determine whether an auditory reminder is timely. The patient portal front-end layer 216-C may access the medications layer 212-A to receive/retrieve prescription data corresponding to the patient. The smart bottle front-end layer 216-D and the digital pill organizer front-end layer 216-E may access the medication layer 212-A.

In some embodiments, the mobile application front-end layer 216-A may include instructions for migrating patient information from a patient computing device (e.g., the patient computing device 104 of FIG. 1). For example, the patient mobile application front-end layer 216-A may include a legacy computing application. The patient may install a non-legacy computing application via the mobile application front-end layer 216-A. The non-legacy computing application may include instructions for retrieving stored patient profile information including existing schedules, medications, and prescriptions. The non-legacy computing application may include instructions for transmitting the retrieved stored patient profile information to another layer of the cloud environment 200. For example, the schedules layer 212-B may receive/retrieve the profile information and store the information in cloud-accessible storage (e.g., the database 150 of FIG. 1). The non-legacy application may download the stored information and present the user with schedules, notifications and lists of medication corresponding to the retrieved stored profile information, as discussed herein.

It should be appreciated that the front-end sub-layers 214 are depicted for explanatory purposes, and that over time, additional layers and/or interfaces may be added. For example, in some embodiments, the front-end sub-layers 214 may include a third-party prescription adherence front-end. Herein the term "front-end" may include applications accessing the take-two layer 210 that include one or more graphical user interfaces and/or those applications that include no graphical user interfaces (i.e., headless front-end applications).

It should be further appreciated that the cloud computing architecture 200 is a global platform capable of being adapted to use by retail pharmacy operations in differing global environments. The cloud computing architecture 200 may be shared across brands and geographies. Multiple instances of the cloud computing architecture 200 may be implemented, for example using multiple instances of some or all of the components of the computing environment 100. For example, in an embodiment, a first cloud computing architecture 200 may be implemented in a first pharmacy computing system 102 in a particular cloud computing region/data center (e.g., North Central United States). A second cloud computing architecture 200 may be implemented in a second pharmacy computing system 102 in a particular, potentially differing, cloud computing region/data center (e.g., Northern Europe). Each of the two cloud computing architectures may be configured independently to account for varying laws/regulations (e.g., Health Insurance Portability and Accountability Act (HIPAA), General Data Protection Regulations (GDPR), etc.). Therefore, the present techniques advantageously improve retail pharmacy computing systems by increasing the flexibility of such systems. In globally-distributed pharmacy computing systems, data sources and systems of record may vary according to geography and/or brand. In some embodiments, the digital decoupling layer 208 may be modified to reduce the amount of customization needed for each instance.

Exemplary Automated Cloud-Based Prescription Reminder Scheduling

Figure 3:
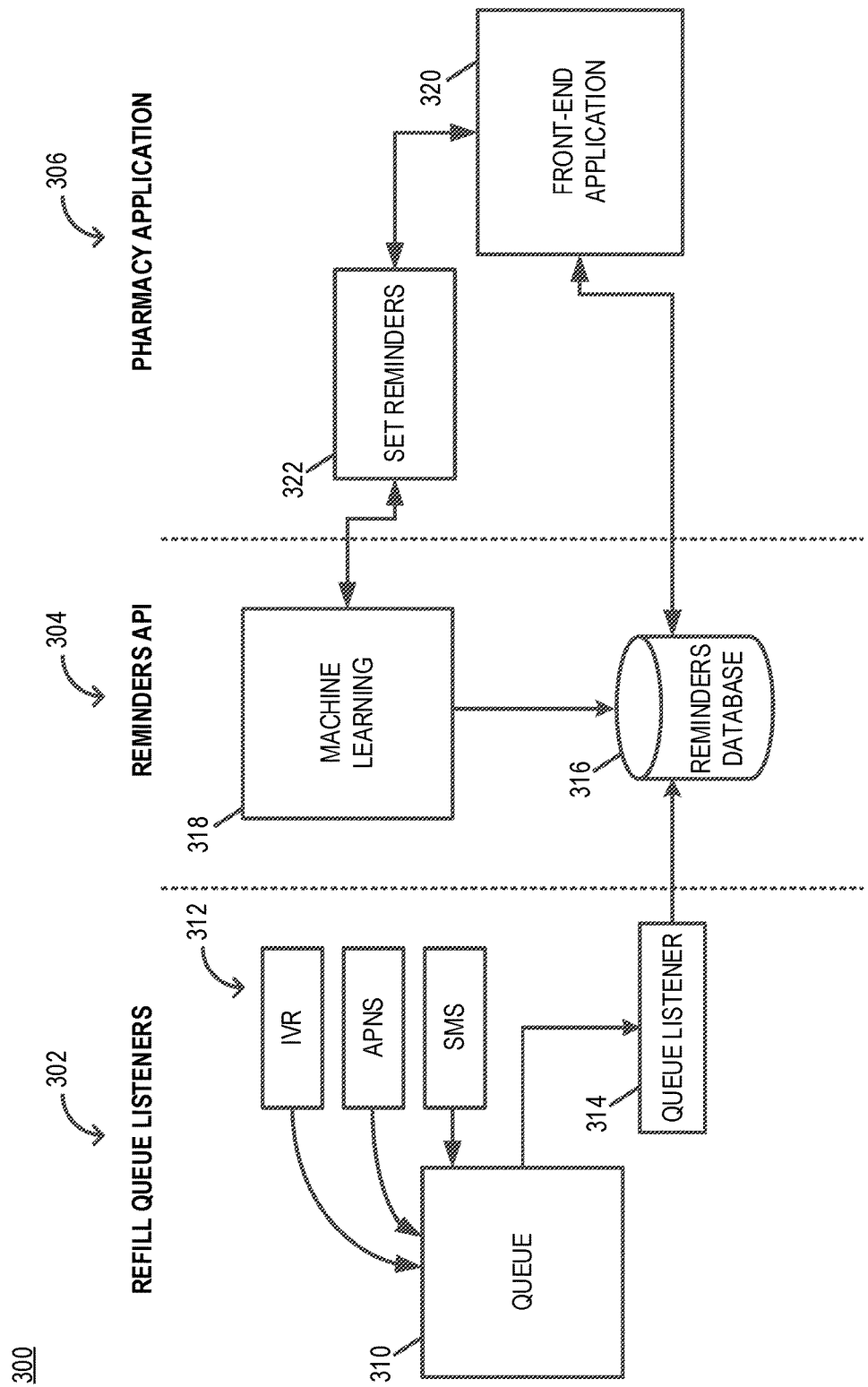
FIG. 3 depicts an exemplary architectural diagram for automated prescription reminder scheduling, according to one embodiment.

FIG. 3 depicts an exemplary architectural diagram of an automated prescription reminder scheduling environment 300, according to one embodiment. The environment may be divided according to a physical and/or logical separation into a fill/refill queue listener region 302, a reminders API region 304 and a front-end application region 306. Within the refill queue listener region 302, a queue 310 may receive fill/refill requests from one or more external messaging systems 312 (e.g., an interactive voice response (IVR) system, a short message service (SMS) system, an Apple push notifications service (APNS) system, etc.). The requests may be events, as discussed with respect to FIG. 2.

A queue listener 314 may dequeue prescription fill/refill events from the queue 310. The queue listener 314 may process the fill/refill events (e.g., via the scheduling module 136 of FIG. 1). The queue listener 314 may generate a reminder schedule and store the reminder schedule in an electronic database 316 in association with the patient's profile. The front-end application region 306 may include a machine learning module 318 including instructions for retrieving/receiving and analyzing the fill/refill events stored in the electronic database 316. For example, the machine learning module 318 may include one or more machine learning model trained by a machine learning training module (e.g., the machine learning training module 130 of FIG. 1). The trained machine learning model may have been previously trained using historical fill/refill event information to generate an initial prescription schedule for the patient. The machine learning module 318 may include one or more further machine learning models trained to generate an updated prescription schedule based on one or more indication of the patient's consumption of medication corresponding to a pharmacy prescription. For example, the further machine learning models may accept as input the initial prescription schedule and one or more indication of the patient's medication consumption (e.g., timestamped metadata corresponding to the patient's consumption received from the patient computing device 104, the connected device 106, etc.).

The front-end application region 306 may include a mobile application 320 that accesses one or more stored reminders 322 in the electronic database 316. The mobile application 320 may display GUIs allowing the patient to review and confirm reminders, as depicted in FIG. 4A and FIG. 4B. The mobile application 320 may register reminders with a scheduling application of the patient mobile device (e.g., a device-specific Calendar API). In some embodiments, the mobile application 320 may synchronize the patient's stored reminders from the electronic database 316 with a local electronic database (not depicted). The mobile application 320 may include instructions for performing a two-way synchronization when any change occurs to the electronic database 316 and/or the local database, in real-time, to keep the patient's reminders current across all devices.

In some embodiments, the stored reminders 322 may include instructions for accessing one or more trained machine learning model in the machine learning module 318 to generate one or more prescription reminders. For example, the stored reminders 322 may include instructions for providing a prescription to the trained machine learning model, and receiving an output corresponding to an electronic calendar object including one or more prescription reminders. The stored reminders 322 may include instructions for transmitting the electronic calendar object to a computing device (e.g., the patient computing device 104) using a suitable messaging technique.

Elements of the environment 300 may implemented in the environment 100. For example, the queue 310 and queue listener 314 may be implemented as modules within the memory 122 of the pharmacy computing system 102, for example. The reminder database 316 may correspond to the database 150 in some embodiments. In some embodiments, the automated prescription reminder scheduling environment 300 may automatically perform scheduling setup for reminders when the patient fills a new prescription and/or refills an existing prescription. The reminder may be displayed in a graphical format and may include information such as when to take the medication, at what time to take the medication, whether to take the medication with food, etc.
Exemplary Cloud-Based Prescription Reminder Graphical User Interfaces FIG. 4A depicts an exemplary computing environment 400 including a reminder configuration push notification GUI 402 and a reminder configuration SMS notification GUI 404. A module of computer-executable instructions executing in a mobile device of the patient, such as the patient computing device 104 of FIG. 1, may cause the GUI 400 and the GUI 402 to be displayed in the patient computing device 104. The module may accept input from the patient, such as textual input, swipe actions, etc. The GUI 402 and the GUI 404 may display one or more notifications transmitted to the patient computing device 104 by the pharmacy computing system 102. It should be appreciated that in some embodiments, the notifications may include information intended to capture the patients attention, such as a notification sound, a pill image, an emphasized medication/take instruction, etc. In some embodiments, the notifications may be displayed in a wearable device (e.g., a smart watch) of the patient.

For example, a module of the patient computing device 104 may cause the GUI 402 and/or the GUI 404 to be displayed in response to the patient picking up a filled/refilled prescription from the patient's local pharmacy. In particular, the pharmacy may input a picked up input into a computing device at the local pharmacy. The pharmacy computing device may cause an event to be propagated via the API 206, as discussed in FIG. 2. For example, in some embodiments, when the patient marks a prescription as filled/refilled, a quantity field corresponding to the prescription in the pharmacy retail computing system may increment an available pill count. Further, when the number of pills begins to run low (e.g., decreases below five available) an event may be generated.

The event may be queued as discussed with respect to FIG. 3. The queue listener may analyze the patient's profile to determine whether the patient has opted in to push notifications. When the patient has opted in, the pharmacy computing device may cause a push notification 406 to be transmitted via the network 108 to the patient computing device 104, and displayed on the computing device of the patient. The push notification 406 may include a payload corresponding to the filled/refilled prescription, the amount remaining, etc. The push notification 406 may include a "refill now" button that when accessed by the patient, causes a refill request to be transmitted to the pharmacy computing system 102 for handling by, for example, the refill queue 310. When the patient has not opted in to push notifications, the pharmacy computing device may cause an SMS message 408 and/or an SMS message 412 to be transmitted to the patient computing device 104, corresponding to the GUI 404.

For example, the SMS 408 and the SMS 414 may include a respective link 410 and link 412. The links may refer to instructions stored within the pharmacy computing system 102. When accessed by the patient, the link 410 and the link 414 may cause the stored instructions to execute in the pharmacy computing system 102. Specifically, when the patient accesses the link, the patient computing device may cause a confirmation request to be transmitted (e.g., to the pharmacy computing system 102). It should be appreciated that the depicted example link 410 may be implemented using any suitable means that allow the patient to express confirmation (e.g., a button, an OK/Cancel dialog box, etc.).

When the patient accesses the link, the patient computing device may cause a create reminder GUI 420 to be displayed, with one or more fields of the create reminder GUI 408 populated with information regarding the filled/refilled prescription, as depicted in FIG. 4B. For example, the create reminder GUI 420 includes prescription information 422, including a medication name, a medication dosage, a medication form and/or instructional information. Additional information (e.g., any SIG code information) may be depicted, in some embodiments. For example, the GUI 420 may include a graphical depiction 424 of the medication. In the depicted example, the graphical depiction 424 includes pill marking information that may advantageously assist the patient in not misidentifying the medication. The GUI 420 may include an image capture element 426 that allows the patient to photograph a medication. In some embodiments, the present techniques may include analyzing the captured photograph (e.g., using a trained machine learning model) to identify the medication.

The GUI 420 may further include scheduling information, including a day of week schedule 428 and a time of day schedule 430. In some embodiments, a module of the patient computing device may set the schedule based on a most common schedule for other patients taking the same medication. In still further embodiments, the schedule may be adjusted according to the patient's history, as discussed below. The scheduling information may include an instruction schedule 432 and a save button 434.

When the patient/caregiver accesses the save button 434 the information in the create reminder GUI 420 may be transmitted to the pharmacy computing system 102. The pharmacy computing system 102 may store the reminder in association with the patient's profile (e.g., in an electronic database such as the database 150 of FIG. 1). Prior to pressing the save button 434, the patient may edit any of the reminder field information. The client application may include computer-executable instructions for accessing remote databases (e.g., a library of bindings for accessing relational databases). The application may authenticate the patient using a suitable authentication scheme (e.g., a username and a password) so that the identity of the patient is known and can be associated with reminders. It should be appreciated that in some embodiments, the reminder may be populated and stored without patient input/acknowledgment.

In some embodiments, the patient may view saved prescriptions in a saved reminders GUI 440, as depicted in FIG. 4C. The saved reminders GUI 440 may include a new reminder element 442 that when selected by the patient, causes the create reminder GUI 420 to be displayed. The create reminder GUI 420 may include information from one or more sig code representations. For example, a quantity of the sig code may be inserted (i.e., interpolated) into a field of the GUI 420.

The GUI 440 may further include a daily reminder panel 444, including a reminder time 446 and a taken indicator 448. The patient/caregiver may select the taken indicator 448 to convey that the patient has taken the medication corresponding to the reminder time 446. The reminder panel 444 may include prescription information 450 that may correspond to the prescription information 422 of FIG. 4B, in some embodiments. The reminder panel 444 may further include a status indicator 452 graphically representing whether the patient has taken the medication corresponding to the reminder time 446.

In some embodiments, additional graphical elements (not depicted) may be used, along with additional instructions. For example, the GUI 440 may include a snooze button. The snooze button may be displayed in a prescription reminder notification, for example, at the patient's daily scheduled time for taking the medication. When the user selects the snooze button, the GUI 440 may transmit a snooze indicator to the pharmacy computing system 102. The snooze indicator may be stored in the database 150. In some embodiments, the snooze indicator may be provided to a trained machine learning model, and analyzed by the trained model to determine an updated schedule.

The GUI 440 may further include a weekly reminder panel 454, depicting one or more days of the week 456. The days of the week 456 may include one or more selected items 458 corresponding to days in which the patient took the medication corresponding to the prescription information 450. The selected items 458 may reflect the patient's selection of the taken indicator 448. In some embodiments, the selected items 458 may reflect information indicating the patient's having taken the prescription obtained via other means (e.g., via a smart bottle cap). In some embodiments, the taken indicator 448 element may be displayed in another format suitable for collecting the patient's confirmation or lack of confirmation. For example, the taken indicator 448 may be displayed in the status bar of a notification overlay of the mobile computing device of the patient.

The GUI 440 may further include a manage medications element 460, including a summary of each of the patient's medications. In some embodiments, only those medications for which reminders are active may be displayed in the manage medications element 460.

The GUI 420 further includes prescription information corresponding to the prescription information 410-A to 410-C of the GUI 408. The GUI 420 includes daily take history 430 indicating whether the prescription was taken and the time at which the prescription was taken. The GUI 420 includes weekly take history 432, visually representing whether the patient took or did not take the prescription on a given day of the week.

In some cases, the prescription may be taken less frequently than daily. In such cases, the weekly take history 432 may include fewer elements, and/or some of the elements may be disabled, reflecting that the patient was not intended to take the medication on one or more day. Further, the depicted example is simplified for explanatory purposes, and in some cases, the GUI may include more complex elements, reflecting more complex medication instructions/schedules. For example, some medications (e.g., a birth control medication) may include a cyclical schedule, such that the patient is instructed to take the medication for a number of days, then abstain for a number of days. In embodiments wherein the instructions call for the patient to take the medication less frequently than every day, and/or multiple times per day, and/or cyclically, the GUI 420 may include according changes. Further, the pharmacy computing system modules may send reminders, awards and other notifications to the patient fewer than once per day, and/or more frequently than once per day.

The GUI 420 may further include a summary list of medications 436 that include the medication summary information and corresponding frequency information. The patient may view the summary list in each of the patient's devices, and any changes are synchronized to the devices in real time. Further, if the patient loses, breaks, sells or otherwise disposes of a patient device, the patient's reminders are advantageously stored in the environment 100 (e.g., in the pharmacy computing system 102), negating the possibility that the patient's information stored in a single device will be lost when the patient no longer has access to a device, as in conventional systems.

Exemplary Machine Learning-Based Adaptive Reminders

As discussed above, the patient may receive automated prescription reminders after filling/refilling a prescription. Further, as noted, the patient may manually select a taken indicator 448 to indicate that the patient has taken or not taken the medication. And in some embodiments, evidence (and timing) of the patient's medication consumption may be collected automatically from the connected device 106. In either case, an indication of the patient's consumption of medication may be transmitted to, and stored by, the pharmacy computing system 102. The ML operation module 132 may analyze collected indications to determine whether the patient's take history corresponds to an existing reminder schedule, and/or to generate a new schedule more in line with the patient's actual behavior. Specifically, the GUI 402 may include instructions for transmitting an indication of the patient's confirmation to a remote computing device (e.g., to the history module 134 of the pharmacy computing system 102 of FIG. 1). The history module 134 may, in turn, store the confirmation, such that over time, the patient's adherence to the prescription regimen may be determined by analyzing the history of confirmations.

The present techniques may include training one or more ML model to generate suggested medication reminder schedules for a particular patient based on analyzing historical patient adherence data. For example, the patient may initially set the patient's reminders to occur at 7:30 AM each morning. The ML model may determine that the patient takes the medication closer to 7:45 AM. The ML model may then prompt the patient/caregiver to adjust the schedule to the later time. In some embodiments, the ML model may automatically adjust the patient's schedule in accordance with the later time.

For example, the patient's activity may generate the following historical adherence data:

| | | Source |
|---|---|---|
| Day | Consumed Time | Source |
| 1 | 7:30 AM | Patient app confirmation |
| 2 | 7:42 AM | Patient app confirmation |
| 3 | 7:46 AM | Smart bottle |
| 4 | 7:40 AM | Patient app confirmation |
| 5 | 7:47 AM | Smart bottle |

Based on the above adherence data, the ML model may determine an appropriate new take time of 7:45 AM. Thus, the present techniques are advantageously able to form a more suitable schedule for a patient, given the history of the patient's actual prescription take activity, using signals from one or more devices within a computing environment (e.g., the computing environment 100 of FIG. 1). The present techniques learn the patient's patterns and routines, improving the patient's schedule. In this way, the present techniques vastly improve conventional pharmacy reminder systems by seamlessly improving patient schedules, without requiring patient input.

In some embodiments, the historical adherence data may include snooze information. The snooze information may be analyzed by a trained machine learning model as a signal that the user wants to delay the taking of the medication. The machine learning model may include instructions for predicting whether the user is snoozing the taking of the medication for preferential reasons (e.g., to a later time in the day) or for reasons related to avoidance of the medication (e.g., due to side effect).

Exemplary Computer-Implemented Methods

Figure 5:
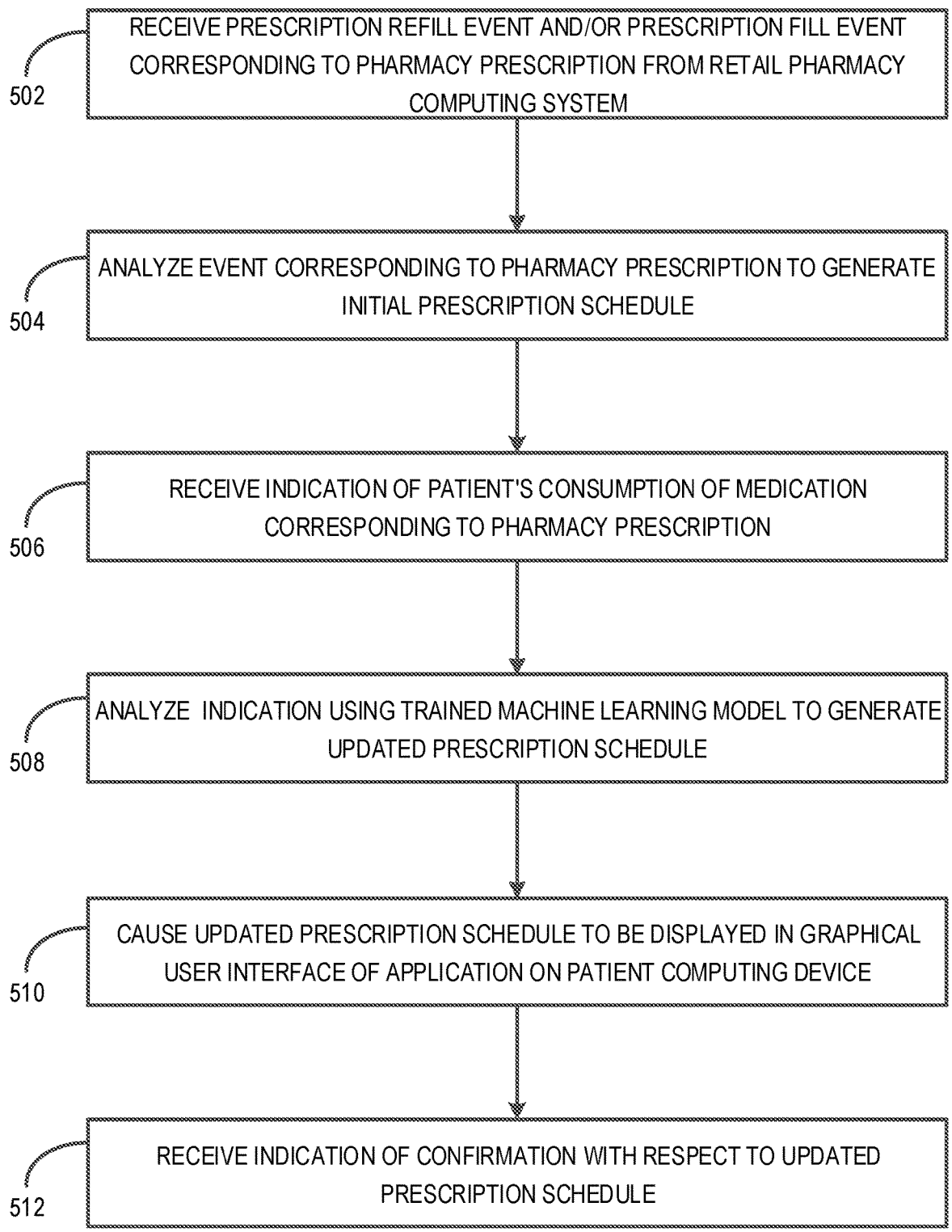
FIG. 5 depicts an exemplary computer-implemented method for facilitating an adaptive reminder of a pharmacy prescription, according to one embodiment and scenario.

FIG. 5 depicts a flow diagram of an exemplary computer-implemented method 500 for facilitating an adaptive reminder of a pharmacy prescription, according to one embodiment. The method 500 may include receiving, from a retail pharmacy computing system, one or both of (i) a prescription refill event, and (ii) a prescription fill event corresponding to the pharmacy prescription (block 502). For example, the retail pharmacy computing system may correspond to the pharmacy computing system 102 of FIG. 1. The prescription refill event and/or prescription fill event may be generated by the retail pharmacy computing system layer 204 of FIG. 2, for example. The event may transit the API 206 and be received by the digital decoupling layer 208. The digital decoupling layer 208 may process the event and dispatch the event to the take-two layer 210.

Depending on the event type, the take-two layer 210 may process the event using one or more of the sub-layers 212. For example, when the event is a fill event or a refill event, the schedules layer 212-B may generate a schedule for the patient based on the event criteria and/or parameters. Other event types may be generated by the pharmacy computing system layer 204 and the front-end sub-layers 214. Events may pass bidirectionally between the pharmacy computing system layer 204 and the front-end sub-layers 214 via the digital decoupling layer 208 and the API 206.

For example, the method 500 may include analyzing the event corresponding to the pharmacy prescription to generate an initial prescription schedule (block 504). Analyzing the event may include analyzing information in a sig code associated with/embedded within the event, such as drug form, frequency, quantity, etc. The method 500 may include storing the initial prescription schedule in the electronic database 150, for example. Once the schedule is created, the scheduling module 136 of FIG. 1 may periodically transmit prescription reminders to the patient's computing device 104 for display and/or further configuration, as depicted in FIG. 4A, FIG. 4B and FIG. 4C.

The method 500 may include receiving one or more indications of the patient's consumption of a medication corresponding to the pharmacy prescription (block 506). In some embodiments, the indication of the patient's consumption may correspond to an event generated by, for example, the mobile computing application front-end layer 216-A. The event may be generated when the patient accesses the taken indicator 448 to indicate that the patient has taken the medication corresponding to the pharmacy prescription. The indications may be received by the history layer 212-C and stored in the electronic database 150, for example. In some embodiments, the indication of the patient's consumption may be an event generated by the connected device 106.

The method 500 may include analyzing the one or more indications of the patient's consumption of the medication using a trained machine learning model to generate an updated prescription schedule (block 508). In some embodiments, the analyzing may be performed only after a predetermined number of indications has been received (e.g., ten or more). Training the machine learning model may be performed before the patient's consumption history is analyzed. The training process may include supervised learning, wherein the prescription consumption history of many patients is analyzed to determine scheduling patterns in patient medication consumption. For example, the machine learning model may be trained to assign weights to particular times of day based on patient profiles, medication types (e.g., a medication drug form), etc. The trained machine learning model may output a calendar object including an updated schedule. The information within the calendar object representing the prescription schedule may be expressed in absolute time (e.g., a list of days/times) and/or as a list of times relative to an existing prescription (e.g., +/− hours).

The method 500 may include causing the updated prescription schedule to be displayed in a computing device of the patient (block 510). The prescription schedule may be transmitted as an electronic calendar object. The electronic calendar object may be encoded in an existing calendar format and/or one specific to the present techniques. The computing device of the patient may display a notification such as the push notification 406 or the SMS notification 408. The patient may interact with the notification by, for example, accessing a link such as the link 410. The link may refer to instructions within a module (e.g., the scheduling module 136) that cause the notification to become activated with respect to the patient's account. A reminder GUI like the reminder GUI 420 may be displayed in response to the patient's accessing of the notification link.

The method 500 may include receiving an indication of confirmation with respect to the updated prescription schedule (block 512). For example, the indication of confirmation may correspond to an event generated by the reminder GUI 420 when the patient selects the save reminder button 434. In some embodiments, the indication of confirmation may be caused by the patient's accessing the notification link. In some embodiments, the indication of confirmation may include modified parameters (e.g., the patient may enter a modified time of day schedule 430). The patient may perform additional/other functions, including viewing prescription consumption history, receiving reports/awards, and delegation/revocation of permission to one or more caregivers.

As noted, the method 500 may include receiving and analyzing one or more snooze notifications from the patient.

In some embodiments, the method 500 may include migrating data from a legacy application to an application executing within the memory of the patient computing device. For example, the method 500 may include retrieving patient profile information (e.g., a list of prescriptions and customized schedules) from the legacy application. The method 500 may include transmitting the retrieved profile information to the pharmacy computing system 102. The pharmacy computing system 102 may include instructions for receiving and storing the profile information in association with the patient (e.g., by using a patient identifier). The pharmacy computing system 102 may make available the profile information, to other components/layers of the computing environment 100 and the computing architecture 200. A cloud-accessible application may display the profile information, to generate reminders and notifications for the patient, as described herein.

In this way, the present techniques improve over conventional non-cloud-enabled techniques, by eliminating a single device architecture. Thus, the patient is able to keep distributed copies of the patient's profile information, and/or a centralized copy, improving data redundancy and backup capabilities. Another positive effect is to improve synchronization, by mirroring the scheduling and notifications relating to the patient's prescribed medications across multiple patient devices.

Additional Considerations

The following considerations also apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of ordinary skill in the art will appreciate still additional alternative structural and functional designs for implementing the techniques disclosed herein through the principles disclosed herein. Thus, while particular embodiments and applications have been illustrated and described, it is to be understood that the disclosed embodiments are not limited to the precise construction and components disclosed herein. Various modifications, changes and variations, which will be apparent to those of ordinary skill in the art, may be made in the arrangement, operation and details of the method and apparatus disclosed herein without departing from the spirit and scope defined in the appended claims.

What is claimed:

1. A regional pharmacy cloud computing system for facilitating an adaptive reminder of a pharmacy prescription, the regional pharmacy cloud computing system comprising:
   one or more processors;
   a retail pharmacy computing system layer communicatively connected to the one or more processors;
   a patient computing device layer communicatively connected to the one or more processors; and
   a memory storing instructions that, when executed by the one or more processors, cause the regional pharmacy cloud computing system to:
      receive, from the retail pharmacy computing system layer, one or both of (i) a prescription refill event, and (ii) a prescription fill event corresponding to the pharmacy prescription,
      analyze the event corresponding to the pharmacy prescription to generate an initial prescription schedule,
      receive, from the patient computing device layer, one or more indications of the patient's consumption of a medication corresponding to the pharmacy prescription,
      analyze the one or more indications using an artificial neural network to generate an updated prescription schedule,
         wherein the artificial neural network is iteratively trained by processing historical prescription consumption information to determine scheduling patterns,
         wherein the artificial neural network comprises a multi-layered network architecture, each layer in the multi-layered network architecture being associated with one or more of: (i) an activation function, (ii) a loss function, or (iii) an optimization function, and
         wherein training the artificial neural network produces one or more weights derived from the historical prescription consumption information, values of the weights being used to iteratively train the trained artificial neural network,
      cause the updated prescription schedule to be displayed in a graphical user interface of an application on the patient computing device layer, and receive an indication of confirmation with respect to the updated prescription schedule, wherein:

the regional pharmacy cloud computing system comprises (i) a first regional pharmacy cloud computing system implemented at a first geographical cloud computing data center corresponding to a first region and (ii) a second regional pharmacy cloud computing system implemented at a second geographical cloud computing data center corresponding to a second region, and the first regional pharmacy cloud computing system is configured independently from the second regional pharmacy cloud computing system.

2. The regional pharmacy cloud computing system of claim 1, the memory storing further instructions that, when executed by the one or more processors, cause the regional pharmacy cloud computing system to:

receive the event corresponding to the pharmacy prescription by analyzing an input sig code.

3. The regional pharmacy cloud computing system of claim 1, the memory storing further instructions that, when executed by the one or more processors, cause the regional pharmacy cloud computing system to:

receive the one or more indications of the patient's consumption of the medication corresponding to the pharmacy prescription from a connected pharmacy device.

4. The regional pharmacy cloud computing system of claim 1, the memory storing further instructions that, when executed by the one or more processors, cause the regional pharmacy cloud computing system to:

receive one or both of (i) a delegation of permission, and (ii) a revocation of permission with respect to one or more caregivers.

5. The regional pharmacy cloud computing system of claim 1, the memory storing further instructions that, when executed by the one or more processors, cause the regional pharmacy cloud computing system to:

generate one or more awards by analyzing the indications of the patient's consumption of the medication corresponding to the pharmacy prescription; and transmit the one or more awards to the patient computing device layer.

6. The regional pharmacy cloud computing system of claim 1, the memory storing further instructions that, when executed by the one or more processors, cause the regional pharmacy cloud computing system to:

receive a snooze indication corresponding to the medication corresponding to the pharmacy prescription.

7. The regional pharmacy cloud computing system of claim 1, the memory storing further instructions that, when executed by the one or more processors, cause the regional pharmacy cloud computing system to:

receive existing patient profile information from a legacy computing application of the patient computing device layer; and display the patient profile information in the graphical user interface of the application on the patient computing device layer.

8. A computer-implemented method for facilitating an adaptive reminder of a pharmacy prescription, comprising:

receiving, from a retail pharmacy computing system layer of a regional pharmacy cloud computing system, one or both of (i) a prescription refill event, and (ii) a prescription fill event corresponding to the pharmacy prescription;

analyzing the event corresponding to the pharmacy prescription to generate an initial prescription schedule;

receiving, from a patient computing device layer of the regional pharmacy cloud computing system, one or more indications of the patient's consumption of a medication corresponding to the pharmacy prescription;

analyzing the one or more indications using an artificial neural network to generate an updated prescription schedule, wherein the artificial neural network is iteratively trained by processing historical prescription consumption information to determine scheduling patterns, wherein the artificial neural network comprises a multi-layered network architecture, each layer in the multi-layered network architecture being associated with one or more of: (i) an activation function, (ii) a loss function, or (iii) an optimization function, and wherein training the artificial neural network produces one or more weights derived from the historical prescription consumption information, values of the weights being used to iteratively train the trained artificial neural network;

causing the updated prescription schedule to be displayed in a graphical user interface of an application on the patient computing device layer; and receiving an indication of confirmation with respect to the updated prescription schedule, wherein:

the regional pharmacy cloud computing system comprises at least (i) a first regional pharmacy cloud computing system implemented at a first geographical cloud computing data center corresponding to a first region and (ii) a second regional pharmacy cloud computing system implemented at a second geographical cloud computing data center corresponding to a second region, and the first regional pharmacy cloud computing system is configured independently from the second regional pharmacy cloud computing system.

9. The computer-implemented method of claim 8, further comprising:

receiving the event corresponding to the pharmacy prescription by analyzing an input sig code.

10. The computer-implemented method of claim 8, further comprising:

receiving the one or more indications of the patient's consumption of the medication corresponding to the pharmacy prescription from a pharmacy connected device.

11. The computer-implemented method of claim 8, further comprising:

receiving one or both of (i) a delegation of permission, and (ii) a revocation of permission with respect to one or more caregivers.

12. The computer-implemented method of claim 8, further comprising:

generating one or more awards by analyzing the indications of the patient's consumption of the medication corresponding to the pharmacy prescription; and transmitting the one or more awards to the patient computing device layer.

13. The computer-implemented method of claim 8, further comprising:

receiving a snooze indication corresponding to the medication corresponding to the pharmacy prescription.

14. The computer-implemented method of claim 8, further comprising:
receiving existing patient profile information from a legacy computing application of the patient computing device layer; and
displaying the patient profile information in the graphical user interface of the application on the patient computing device layer.

15. A non-transitory computer readable medium containing program instructions that when executed, cause a computer to:
receive, from a retail pharmacy computing system layer of a regional cloud computing system, one or both of (i) a prescription refill event, and (ii) a prescription fill event corresponding to the pharmacy prescription;
analyze the event corresponding to the pharmacy prescription to generate an initial prescription schedule;
receive, from a patient computing device layer of the regional cloud computing system, one or more indications of the patient's consumption of a medication corresponding to the pharmacy prescription;
analyze the one or more indications using an artificial neural network to generate an updated prescription schedule,
wherein the artificial neural network is iteratively trained by processing historical prescription consumption information to determine scheduling patterns,
wherein the artificial neural network comprises a multi-layered network architecture, each layer in the multi-layered network architecture being associated with one or more of: (i) an activation function, (ii) a loss function, or (iii) an optimization function, and
wherein training the artificial neural network produces one or more weights derived from the historical prescription consumption information, values of the weights being used to iteratively train the trained artificial neural network;
cause the updated prescription schedule to be displayed in a graphical user interface of an application on the patient computing device layer; and
receive an indication of confirmation with respect to the updated prescription schedule,
wherein:
the regional pharmacy cloud computing system comprises at least (i) a first regional pharmacy cloud computing system implemented at a first geographical cloud computing data center corresponding to a first region and (ii) a second regional pharmacy cloud computing system implemented at a second geographical cloud computing data center corresponding to a second region, and
the first regional pharmacy cloud computing system is configured independently from the second regional pharmacy cloud computing system.

16. The non-transitory computer readable medium of claim 15 containing further program instructions that when executed, cause a computer to:
receive the event corresponding to the pharmacy prescription by analyzing an input sig code.

17. The non-transitory computer readable medium of claim 15 containing further program instructions that when executed, cause a computer to:
receive the one or more indications of the patient's consumption of the medication corresponding to the pharmacy prescription from a connected pharmacy device.

18. The non-transitory computer readable medium of claim 15 containing further program instructions that when executed, cause a computer to:
receive one or both of (i) a delegation of permission, and (ii) a revocation of permission with respect to one or more caregivers.

19. The non-transitory computer readable medium of claim 15 containing further program instructions that when executed, cause a computer to:
generate one or more awards by analyzing the indications of the patient's consumption of the medication corresponding to the pharmacy prescription; and transmit the one or more awards to a mobile computing device of the patient.

20. The non-transitory computer readable medium of claim 15 containing further program instructions that when executed, cause a computer to:
receive a snooze indication corresponding to the medication corresponding to the pharmacy prescription.

* * * * *